United States Patent
Prow et al.

(10) Patent No.: US 9,662,095 B2
(45) Date of Patent: May 30, 2017

(54) MICROBIOPSY DEVICE

(71) Applicant: THE UNIVERSITY OF QUEENSLAND, Queensland (AU)

(72) Inventors: Tarl W. Prow, Sunnybank (AU); H. Peter Soyers, Holland Park (AU); Alexander Bernard Ansaldo, Coorparoo (AU)

(73) Assignee: The University of Queensland, Queensland (AU)

( * ) Notice: Subject to any disclaimer, the term of this patent is extended or adjusted under 35 U.S.C. 154(b) by 0 days.

(21) Appl. No.: 14/394,907

(22) PCT Filed: Apr. 16, 2013

(86) PCT No.: PCT/AU2013/000394
§ 371 (c)(1),
(2) Date: Oct. 16, 2014

(87) PCT Pub. No.: WO2013/155557
PCT Pub. Date: Oct. 24, 2013

(65) Prior Publication Data
US 2015/0112225 A1 Apr. 23, 2015

(30) Foreign Application Priority Data

Apr. 16, 2012 (AU) .............................. 2012901490

(51) Int. Cl.
*A61B 10/00* (2006.01)
*A61B 10/02* (2006.01)
(Continued)

(52) U.S. Cl.
CPC ...... *A61B 10/0096* (2013.01); *A61B 5/15045* (2013.01); *A61B 5/150282* (2013.01);
(Continued)

(58) Field of Classification Search
CPC .......... A61B 5/14532; A61B 5/150442; A61B 5/150458; A61B 5/150282;
(Continued)

(56) References Cited

U.S. PATENT DOCUMENTS 5,928,161 A * 7/1999 Krulevitch ......... A61B 10/0275
600/564
7,255,705 B2 * 8/2007 Hsu ........................ A61B 17/32
30/304

(Continued)

OTHER PUBLICATIONS

Extended European Search Report mailed Apr. 7, 2015 in European Application No. 13778287.6 (7 pages).

(Continued)

*Primary Examiner* — Devin Henson
(74) *Attorney, Agent, or Firm* — Nixon & Vanderhye P.C.

(57) ABSTRACT

A microbiopsy device for taking biological samples, comprising a body including two or more cutting elements for cutting tissue to form a biological sample; and a chamber inside the body for receiving and retaining the biological sample, the chamber having an opening between the cutting elements, wherein the cutting elements are arranged to cut a section of tissue having a width of less than 1 mm.

25 Claims, 12 Drawing Sheets

(51) Int. Cl.
*A61B 17/3205* (2006.01)
*A61B 17/32* (2006.01)
*A61M 37/00* (2006.01)
*A61B 17/3209* (2006.01)
*A61B 17/00* (2006.01)
*A61B 5/15* (2006.01)
*A61B 17/322* (2006.01)
*A61B 17/3211* (2006.01)

(52) U.S. Cl.
CPC ...... *A61B 10/0233* (2013.01); *A61B 10/0266* (2013.01); *A61B 5/150442* (2013.01); *A61B 5/150458* (2013.01); *A61B 17/322* (2013.01); *A61B 17/3211* (2013.01); *A61B 17/32053* (2013.01); *A61B 17/32093* (2013.01); *A61B 2017/00345* (2013.01); *A61B 2017/320064* (2013.01); *A61M 2037/0053* (2013.01); *A61M 2037/0061* (2013.01); *Y10T 29/49826* (2015.01)

(58) Field of Classification Search
CPC ............ A61B 10/0096; A61B 10/0233; A61B 17/322; A61B 17/32053; A61B 17/32093; A61B 17/00345; A61B 2017/00345; A61B 2017/320064; A61M 2037/0053; A61M 2037/0061; Y10T 29/49826

USPC .................................................. 600/583, 584
See application file for complete search history.

(56) References Cited

U.S. PATENT DOCUMENTS

| | | | |
|---|---|---|---|
| 7,740,595 | B2 | 6/2010 | Brown |
| 2004/0175690 | A1 | 9/2004 | Mishra et al. |
| 2007/0100361 | A1 | 5/2007 | Cohen |
| 2007/0106178 | A1* | 5/2007 | Roe .................... A61B 5/14532 600/583 |
| 2007/0219459 | A1 | 9/2007 | Cohen |
| 2008/0167576 | A1* | 7/2008 | Cho .................... A61B 10/0233 600/564 |
| 2010/0049091 | A1* | 2/2010 | Haar .................... A61B 5/1411 600/583 |
| 2012/0116322 | A1 | 5/2012 | Brink et al. |

OTHER PUBLICATIONS

International Search Report for PCT/AU2013/000394, mailed May 21, 2013.

* cited by examiner

MICROBIOPSY DEVICE

This application is the U.S. national phase of International Application No. PCT/AU2013/000394, filed 16 Apr. 2013, which designated the U.S. and claims priority to Australia Patent Application No. 2012901490, filed 16 Apr. 2012, the entire contents of each of which are hereby incorporated by reference.

TECHNICAL FIELD

The present invention relates generally to biopsy devices.

BACKGROUND ART

It is often necessary to take biological samples, such as tissue or blood, from humans or animals to aid in the diagnosis and treatment of various diseases or disorders. Such diseases include skin cancer, inflammatory diseases and infectious diseases, such as mosquito-borne diseases.

Skin cancer currently accounts for 80% of all newly diagnosed cancers, with over 10,300 melanoma cases per year and a combined death toll of 1,850 people per year in Australia alone.

The current standard of care for diagnosing skin cancer is to take a biopsy of the lesion for histological evaluation. However, this is often challenging when patients present with high numbers of lesions which require evaluation.

There are three main types of biopsy: 1) shave biopsy, where section of superficial (2-3 mm deep) skin is removed; 2) conventional punch biopsy, where a circular cutting tool is used to remove 2-4 mm skin pieces up to several millimeters deep; and 3) excision biopsy, the use of a scalpel to remove entire lesion or an area of abnormal skin including a small area of normal skin.

In each case, the amount of tissue removed is significant: such as a width in the order of a few millimeters. In addition, the biopsy operation may require more than one step: in the case of a punch biopsy, the "core" of skin created by the punch must be raised using tweezers or a needle and it must then be cut from the underlying tissue. Moreover, the risks involved in a biopsy procedure can include bleeding, pain, local reaction to the anaesthetic, infection and scarring. These risks multiply with every mole or lesion requiring evaluation.

With regard to diagnosis and treatment of infectious diseases, the frequency of human infections is predicted to increase due to climate change and increased population density. Determining which pathogen is causing an outbreak can be difficult and dangerous, because this traditionally requires blood samples from the ill. Therefore, there is a risk of needle injuries, need for a cold chain to detect infectious pathogens and risks due to the often high level biosafety requirements of these agents.

There is accordingly a need for a biopsy system that overcomes, or at least alleviates one or more of the disadvantages of the prior art.

SUMMARY OF THE DISCLOSURE

In an aspect of the present disclosure, there is provided a microbiopsy device for taking biological samples, comprising a body including two or more cutting elements for cutting tissue to form a biological sample, and a chamber inside the body for receiving and retaining the biological sample, the chamber having an opening between the cutting elements.

The inclusion of a chamber inside the body and between the cutting elements allows for the biological sample to be retained in the chamber immediately after it is formed, thereby enabling the biopsy to be conducted in a single step. In one embodiment, the chamber may be at least partially open-sided.

When taking tissue samples having a small width (eg less than 1-2 mm), it has been found that the inclusion of two or more cutting elements (as compared with a single circular cutting edge of a punch biopsy tool) has been found to assist in the production of a "cored" biological sample, instead of simply creating a puncture hole in the patient's skin.

In an embodiment of the microbiopsy device, the two or more cutting elements are opposed to each other.

The two or more cutting elements may be secured with respect to each other. In such an arrangement, the absence of moving parts can simplify the manufacturing process.

In an embodiment of the microbiopsy device, each cutting element extends from an end of the body.

In an embodiment of the microbiopsy device each cutting element extends from the body by substantially the same distance.

The microbiopsy chamber may have a width from 50 to 200 µm, such as between 100 to 200 µm. In an embodiment, the width is around 150 µm.

In an embodiment of the microbiopsy device, the two or more opposed cutting elements together define at least one cutting edge and more preferably define a substantially continuous cutting edge. This facilitates the cutting and removal of the tissue section.

In an embodiment of the microbiopsy device the two or more opposed cutting elements are arranged to cut a section of tissue having a width of less than 1 mm. This arrangement ensures that a significantly smaller cut is applied to the tissue as compared to conventional biopsy devices, (see FIG. 10 for an illustration) and therefore minimises pain and scarring. Moreover, the small cut means that only a small sample of biological material is taken. This enables many more samples to be taken across a larger area than is currently possible because suturing is unlikely to be necessary. The smaller sample size is also more easily disengaged from the surrounding tissue than a conventional large biopsy sample, meaning that it can be effectively automatically retained in the microbiopsy device's chamber after the sample is formed. This translates into a quicker and more efficient biopsy process than conventional multi step biopsies.

In an embodiment of the microbiopsy device the two or more opposed cutting elements are arranged to cut a section of tissue having a width of less than 750 microns.

In an embodiment of the microbiopsy device the two or more opposed cutting elements are arranged to cut a section of tissue having a width of less than 500 microns.

In an embodiment of the microbiopsy device the two or more opposed cutting elements are arranged to cut a section of tissue having a width of less than 400 microns.

In an embodiment of the microbiopsy device the two or more opposed cutting elements are arranged to cut a section of tissue having a width of less than 300 microns.

In an embodiment of the microbiopsy device the two or more opposed cutting elements are arranged to cut a section of tissue having a width of less than 200 microns.

In an embodiment of the microbiopsy device the two or more opposed cutting elements are arranged to cut a section of tissue having a width between 100 and 200 microns.

In an embodiment of the microbiopsy device, the section of tissue is non circular.
}

In an embodiment of the microbiopsy device, the section of tissue is substantially rectangular.

In an embodiment of the microbiopsy device, each cutting element comprises a tapered section of a plate.

In an embodiment, the microbiopsy device comprises an assembly of at least two plates, wherein each cutting element may be defined by a respective tapered section of one of said plates.

In an embodiment the microbiopsy device comprises an assembly of at least three plates, wherein each plate may provide at least one cutting element. Each plate may have a thickness of less than 100 µm, such as around 50 µm. The overall thickness of the assembly may be less than 200 µm, such as around 150 µm.

In an embodiment the microbiopsy device has a modular design that can be customized for several different applications. For example, the microbiopsy device can be assembled from plates having different functionalities—such as transparent outer plates that enable visual analysis of the sample in the chamber, or absorbent components included in the inner plates that can absorb biological fluids. In an embodiment of the microbiopsy device, the cutting elements of respective outer plates of the assembly are aligned.

In an embodiment of the microbiopsy device, the inner plate/s include cutting elements which may be laterally spaced from the cutting elements of the outer plates.

In an embodiment of the microbiopsy device, the chamber is defined by one or more recesses in the plates.

In an embodiment of the microbiopsy device, the chamber is defined by one or more recesses in the inner plate/s.

In an embodiment of the microbiopsy device, the recesses are located between the cutting elements of the inner plate/s.

The volume of the chamber of the microbiopsy device may be less than $5 \times 10^{-3}$ mm$^3$, such as less than $3 \times 10^{-3}$ mm$^3$. In an embodiment, the volume is approximately $2 \times 10^{-3}$ mm$^3$ such as $1.8 \times 10^{-3}$ mm$^3$.

In an embodiment of the microbiopsy device, the chamber retains the biological sample therein by friction.

The chamber walls may have a surface roughness, $R_A$, less than 25 µm. The surface roughness, $R_A$, may be greater than 1 µm. In an embodiment, the $R_A$ is greater than 5 µm. It has been found that the optimum surface roughness is a balance between sufficient is roughness to frictionally retain the sample therein but not too much roughness such that the surface area available for sample collection in the chamber is significantly decreased.

In an embodiment, the microbiopsy device further includes retaining elements to retain the biological sample therein.

In an embodiment of the microbiopsy device, the retaining elements comprises projections extending from one or more chamber walls. The projections may be provided at the opening of the chamber.

In an embodiment of the microbiopsy device, the retaining elements comprise projections on one or more inner faces of the cutting elements.

In an embodiment of the microbiopsy device, the chamber comprises a non-circular cross section. Without wishing to be limited by theory, it is thought that a non-circular cross section may be important for frictionally retaining a tissue sample in the chamber without the need for retaining elements.

In an embodiment of the microbiopsy device, the chamber comprises a rectangular cross section. While the non-circular cross-section may have any number of sides, a four sided chamber is likely to be simpler to manufacture.

In an embodiment of the microbiopsy device, the biological sample is tissue.

In an embodiment of the microbiopsy device, the biological sample is a biological fluid, such as blood, plasma or serum. In this embodiment, the chamber may contain a biological fluid capturing element, such as an absorbent material, and the biological fluid soaks into the chamber (typically over a period of seconds). The absorbent material may comprise a fibrous material (e.g. filter paper). The fibrous material may be impregnated with chemicals that would lyse cells, denature proteins, and/or protect DNA/RNA. Examples of such a material may be FTA™ cards, polyethersulfone and Whatman (Grade 1) filter paper. In this embodiment, the chamber may be at least partially open sided, for example, the device may include outer plates that include recesses therein to enable (physical and/or visual) access to the absorbent membrane. This embodiment of the microbiopsy device has applications in extracting serum samples from patients for example to characterise viral infections in vivo. After applying the microbiopsy device to a patient using an applicator (eg a plunger), the device can be detached from the applicator and either the absorbent material per se, or the entire device (plus absorbent material) can be placed into a tube containing a stabilising preservative (such as RNALater or PaxGene).

The microbiopsy device can therefore be used as a minimally invasive means to procure samples for molecular diagnostics. This could be useful across the disease spectrum from viral, bacterial, fungal and protozoan infections.

The microbiopsy device may be constructed from a biocompatible material. By "biocompatible" is meant that the material does not cause a toxic, injurious, or adverse immunological response in living tissue. The material may be steel or a polymer of an appropriate medical grade.

In an embodiment of the microbiopsy device, each plate comprises steel.

In an embodiment, the microbiopsy device comprises an insert for a punch biopsy applicator.

In an embodiment, the microbiopsy device includes a securing member for securing the plates in the assembly.

In an embodiment of the microbiopsy device, the securing member comprises a clamp.

In another embodiment, a plurality of microbiopsy devices are provided in an array. The array may comprise devices arranged in columns and rows and can be used for example to take multiple samples simultaneously from skin.

In another aspect there is disclosed a method for making the microbiopsy device including the steps of providing at least two plates, each plate including a tapered section defining one or more respective cutting elements and at least one of the plates including a recess therein, and forming an assembly of the plates such that the cutting elements are opposed from each other and together define a cutting end of the device, and the one or more recesses define a chamber having an opening between the cutting elements.

In an embodiment, the method includes the step of forming the plates from a blank including panels corresponding to the plates. The step of forming the plates may comprise folding the blank between the panels. Alternatively, or in addition, the step of forming the plates may comprise cutting the blank between the panels. The plates may be formed by laser cutting, moulding, die punching or chemical etching. The blank may include two or more panels, each panel may have at least one tapered section which forms one or more of the cutting elements upon assembly, and at least one panel may include a recess wherein the recess or recesses may define the chamber upon assembly.

In an embodiment, the blank may comprise stainless steel.

In another embodiment of the method, the microbiopsy device is formed by molding a plastics material. The plastics material may be a medically approved transparent polymer, such that the device can be used to remove a small piece of skin and then immediately image the sample (such as by reflectance confocal microscopy (RCM), multiphoton microscopy (MPM) or fluorescence lifetime imaging (FLIM) without further preparation. The polymer may need to be transparent to light from 350-900 nm. Depending on the properties of the polymer, it may require additional structural support.

In another aspect, there is provided a method for taking a biological sample from tissue, including a step of applying a microbiopsy device to the tissue, the microbiopsy device comprising a body including two or more cutting elements for cutting the tissue to form the biological sample and a chamber inside the body for receiving and retaining the biological sample, the chamber having an opening between the cutting elements.

The method of taking a biological sample may include applying the microbiopsy device to the tissue at an impact velocity of greater than 9 m/s, such as 13 m/s or higher. In an embodiment, the microbiopsy device is applied at an impact velocity of 15 m/s or higher.

The method of taking a biological sample may include applying a compression force to the tissue prior to applying the microbiopsy device to the tissue. The pre-application skin compression force may be a minimum of 2 N, such as 5N or higher. In an embodiment, the skin compression force is 10N or higher. The maximum pre-application skin compression force may be determined by the natural resistance to damage of the skin. The maximum compression force may be 20N.

The biological sample may be subsequently removed from the device for example by vortexing the device and sample.

Depending on the dimensions and velocity of application of the device, the microbiopsy device may penetrate skin to a depth of 200 μm or higher, such as to a minimum depth of 240 μm. The maximum penetration may exceed 300 μm, such as up to 370 μm.

In another aspect, there is provided a method of diagnosing a condition, including:
using the microbiopsy device of the disclosure to take a biological sample,
diagnosing a condition from the biological sample.

In another aspect, there is provided a method of monitoring the progress of a condition, including:
using the microbiopsy device of the disclosure to take a biological sample,
monitoring a condition in the biological sample.

In another aspect, there is provided a method of treatment of a condition, including:
using the microbiopsy device of the disclosure to take a biological sample,
diagnosing a condition from the biological sample,
treating the condition.

In another aspect, there is provided a diagnostic kit including the microbiopsy device of the disclosure.

Accordingly, the microbiopsy device may be used in one or more methods for diagnosing, monitoring or treating a condition.

In the case of a dermatological condition, the device may be used as follows:

The microbiopsy device is applied to a patient's skin and extracts a tissue sample into the chamber. The device plus sample can then be placed into a Polymerase Chain Reaction (PCR) tube containing a nucleic acid stabilizer such as PAXgene™ (path lab product) or RNAlater® (research lab product). The sample can then be subjected to molecular analysis for a range of conditions.

The small size of the microbiopsy device confers a number of significant benefits over conventional skin biopsy punches. The punch allows for 'suspicious' (potentially cancerous) skin lesions to be regularly sampled in order to diagnose or follow disease progression or to monitor therapeutic benefit. The punch can be used in a number of ways:

Monitoring: The primary clinical application of the punch is as a screening tool for skin cancer. The punch is ideal for sampling naevi (chronic skin lesion—moles, birthmarks etc) for molecular changes across large skin areas. This allows greater sampling of suspicious lesions than what is possible with conventional large skin biopsy punches which have a cutting diameter of eg~3 mm. Each sample can be tested for a specific genetic mutation indicative of melanoma. If a relevant mutation is detected the entire region can be later excised. The sampled material can then be analysed using one or more of the following techniques: polymerase chain reaction, real-time PCR, next generation sequencing, RNASeq, Sanger sequencing, Southern blotting, Northern blotting, Western blotting, Enzyme linked immunoassay, microplate assay, probe hybridization assays, immunohistochemistry, automated protein analysis, 2-D PAGE analysis, microarray, bead based array and in situ hybridization.

Determining therapeutic success: The punch can be used to aid the sampling of naevi to assess therapeutic success of a pharmacological intervention.

Diagnostic: The punch can also be used as a companion diagnostic in conjunction with specific therapeutics.

The key melanoma related mutations that could be detected using molecular analysis are found in the NRAS oncogene and the proto-oncogene, BRAF. Both mutations appear to be mutually exclusive although they both affect the same downstream pathway through MAPK:

NRAS. The most common NRAS mutations are in exon 2 at codon 61, specifically Q61L (leucine substitution for glutamine). The Q61 mutations result in a constitutively active form of the protein leading to uncontrolled cellular proliferation.

BRAF. BRAF is mutated in 40-60% of melanoma samples. The most common BRAF mutation is at codon 600, resulting in the substitution of glutamic acid for valine (V600E mutation). This mutation results in constitutive kinase activity of BRAF and subsequent is downstream signalling through the MAP kinase pathway. The microbiopsy device is an ideal tool to use as a companion diagnostic with a therapeutic such as Zelboraf® (Vemurafenib, Genentech) which is a BRAF inhibitor that is able to block the function of the V600E-mutated BRAF protein.

A number of other melanoma related mutations are present which are less useful for diagnostic purposes. These include KIT (a cell surface tyrosine kinase that plays a central role in normal melanocyte development) and PTEN (a tumour suppressor gene involved in controlling cell cycle progression, cell growth and cell proliferation).

Biological samples extracted from 5 human (non-diseased) subjects using the microbiopsy device are of sufficient quality to enable their subsequent analysis using molecular tools such as PCR. Tests have shown, for example, that 20 +/−8 ng of DNA and 28 +/−6 ng of RNA can be extracted from the samples.

With only 9 ng of microbiopsy DNA, successful melanocortin-1 receptor (MC1R) nested PCR amplification with downstream sequencing can be achieved. This is significant because MC1R is a challenging sequence to amplify due to having a 1 kb highly G-C rich product.

BRIEF DESCRIPTION OF THE DRAWINGS

Notwithstanding any other forms which may fall within the scope of the device and method as set forth in the Summary, specific embodiments will now be described, by way of example only, with reference to the accompanying drawings in which:

FIG. 1(a) shows a part perspective view of a first embodiment of a microbiopsy device;

FIG. 1 (c) (i), (ii), (iii) and (iv) shows plan views of a blank for the first embodiment, a perspective view of the blank assembled to form the first embodiment, and a spring applicator loaded with the first embodiment;

FIG. 2 (b) shows a side view of the second embodiment of a microbiopsy device.

FIG. 2 (c) shows a plan view of an alternative blank for the second embodiment.

FIG. 6(a) shows micrographs of the recess in the inner plates of the microbiopsy devices used in the tests. FIG. 6(b) is a graph of the amount of DNA extracted (ng) versus surface roughness ($R_A$) of chamber walls.

DETAILED DESCRIPTION OF SPECIFIC EMBODIMENTS

Figure 1:
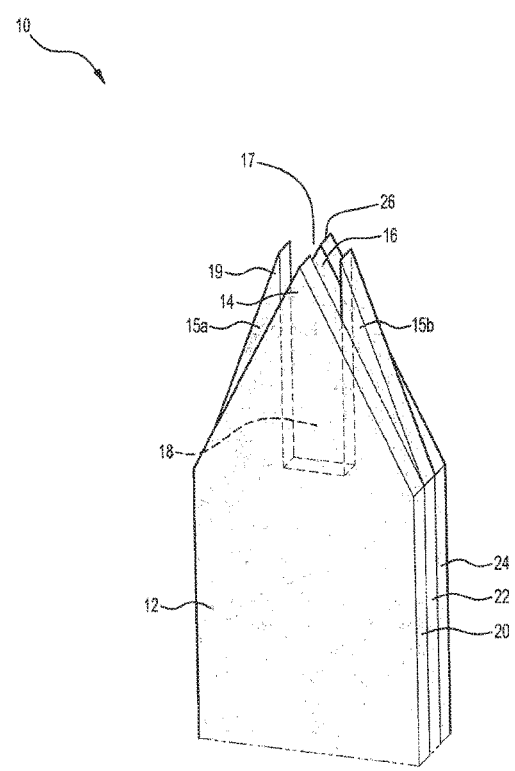
FIG. 1 (b) shows an exploded view of the first embodiment of a microbiopsy device.
Figure 1:
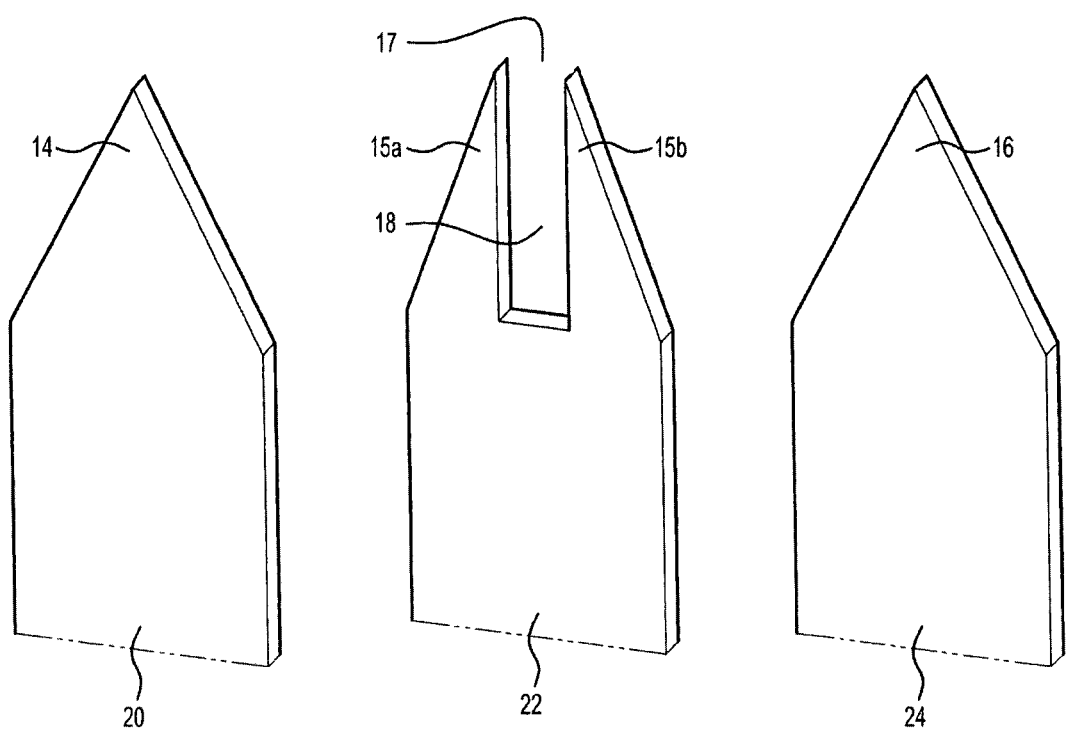
Figure 1:
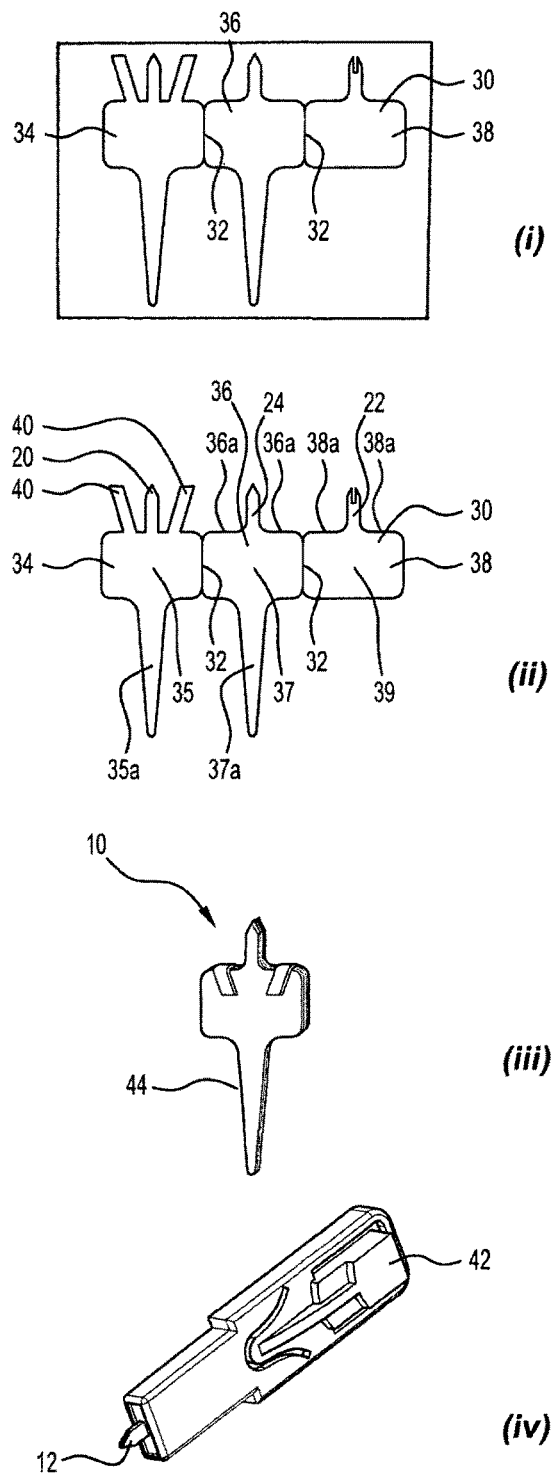

Referring firstly to FIG. 1(a) and FIG. 1(b), a partial perspective view of a first embodiment of a microbiopsy device 10 for taking biological samples is shown. The microbiopsy device 10 comprises an assembly of three surgical grade stainless steel plates 20, 22, 24. The plates are clamped together (not shown) to jointly provide a body 12 from which extends four cutting elements 14, 15a, 15b and 16 which together provide a cutting end 19 for cutting tissue and forming a biological sample (such as a tissue sample). It may be noted that a different number of cutting elements may be provided in other embodiments. Two cutting elements, 14 and 16 comprise respective apices of tapered end sections on the outer plates 20 and 24. The other two cutting elements 15a and 15b each comprise a tapered end region on the inner plate 22. The cutting elements 14 and 16 are axially aligned with each other. The cutting elements 15a and 15b are laterally spaced from the cutting elements 14 and 16. The four cutting elements together define a substantially continuous cutting edge 26.

A chamber 18 (shown in dotted outline in FIG. 1(a)) is provided inside the microbiopsy device 10 for receiving and retaining the tissue sample (not shown). The chamber 18 has an opening 17 between the cutting elements 14, 15a, 15b and 16. As shown in the exploded view in FIG. 1 (b), the chamber is defined by a longitudinal recess 26 between the cutting elements 15a and 15b in the inner plate 22. When the plates are assembled, the chamber 18 is therefore substantially rectangular in cross section.

As shown in the embodiment in FIG. 1, the cutting elements 14, 15a, 15b and 16 extend for a substantially similar distance from the body 12. This configuration ensures that is the points of all four cutting elements contact the skin of a patient at the same time during a biopsy to thereby simultaneously apply points of pressure and result in a precise excision. The cutting elements 14, 15a, 15b and 16 are spaced from each other to enable cutting of a section of tissue with a width of less than 1 mm, such as less than 750 µm. When performing a biopsy, using the device as shown in the embodiment in FIG. 1, cutting elements 14, 15a, 15b and 16 are inserted into tissue using a spring loaded applicator 42, (FIG. 1 (c)). After the tissue is cut by cutting elements 14, 15a, 15b and 16, at least a portion of that tissue is received in the chamber 18 via the opening 17 and is retained in the chamber 18 by friction, as the microbiopsy device 10 is withdrawn from the tissue.

FIG. 1 (c) (i) to (iv) illustrate the formation and use of the first embodiment of a microbiopsy device 10 from a surgical grade stainless steel blank 30. FIG. 1(c) (i) and (ii) show the laser cut blank 30 prior to and after, respectively, removal from a 0.05 mm thick steel sheet. As can be seen, the blank 30 comprises three panels 34, 36 and 38 which respectively include the plates 20, 24 and 22. The three panels are separated by lines 32 along which the panels can be folded or cut then assembled into the microbiopsy device 10, as shown in FIG. 1(c) (iii).

Panels 34, 36 and 38 respectively include enlarged portions 35, 37 and 39. The enlarged portions 35 and 37 respectively include mounting stems 35a and 37a. Panel 34 also includes foldable flaps 40 located either side of plate 20 which can be folded over the shoulders 36a, 38a of panels 36 and 38 in order to secure the assembly of panels together. The enlarged portions 35, 37 and 39 overlap during assembly together form a mounting member 44 which is configured to be received in a spring loaded applicator 42 as shown in FIG. 1 (c) (iv). The mounting member 44 is preferably ejectable from the applicator 42 after use.

In the following descriptions of further embodiments of the microbiopsy device, like reference numerals will refer to like parts and discussion will focus on those features which differ from the first embodiment.

Figure 2:
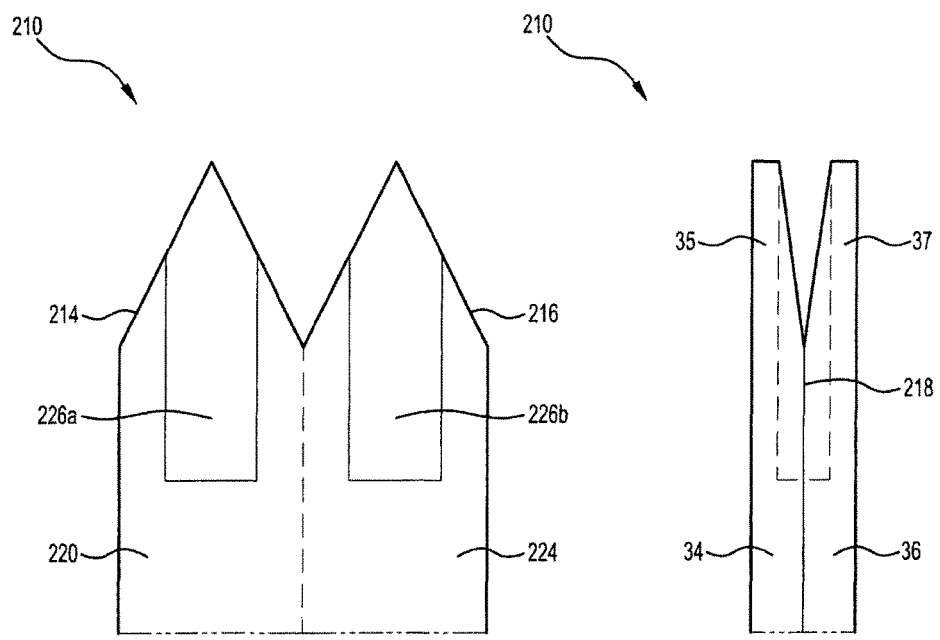
FIG. 2 (a) shows a plan view of a blank for a second embodiment of a microbiopsy device.
Figure 2:
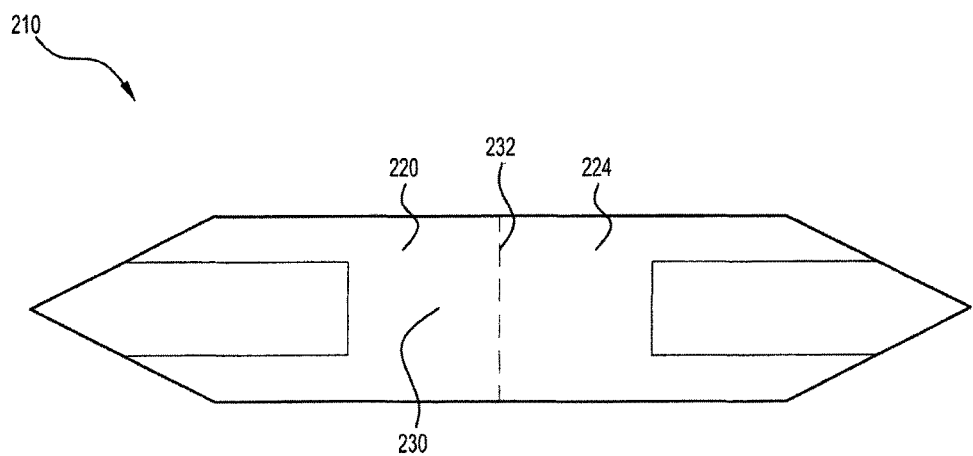

Referring to FIGS. 2(a), 2(b) and FIG. 2(c) a second embodiment of the microbiopsy device 210 is shown. Again, like reference numerals refer to like parts. The microbiopsy device 210 comprises two plates 220 and 224 including respective tapered end sections forming cutting elements 214 and 216. The end section of each plate is tapered depthwise as well as longitudinally. The thus formed cutting elements 220 and 224 are aligned with each other in the assembled biopsy device 210. The plates 220 and 224 include longitudinal channels 226a and 226b which together define a chamber 218 when the plates are assembled into the biopsy device 210.

The microbiopsy device 210 can be assembled from a surgical grade stainless steel is blank 230 that includes plates 220 and 224 and which has been produced by laser cutting. (FIG. 2(c)). The device 210 can be assembled by cutting or folding the blank 230 along line 232 between the cutting elements.

Figure 3:
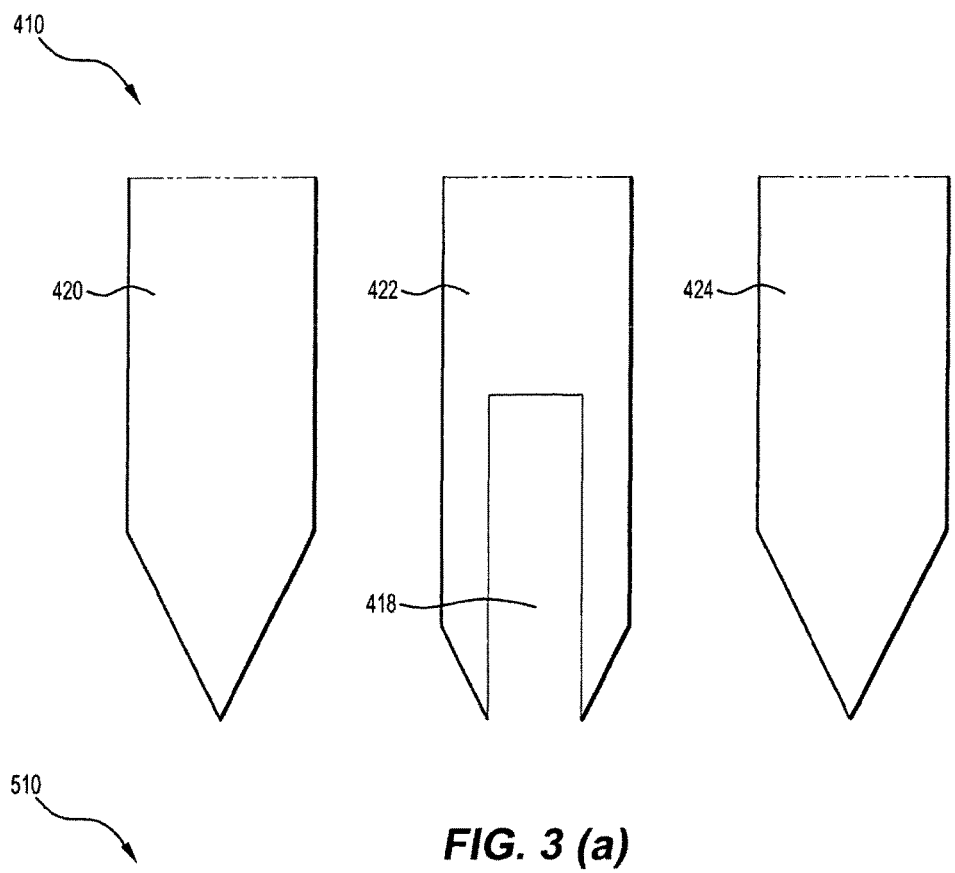
FIGS. 3 (a) and (b) are exploded schematic views of two alternative embodiments of the microbiopsy device.
Figure 3:
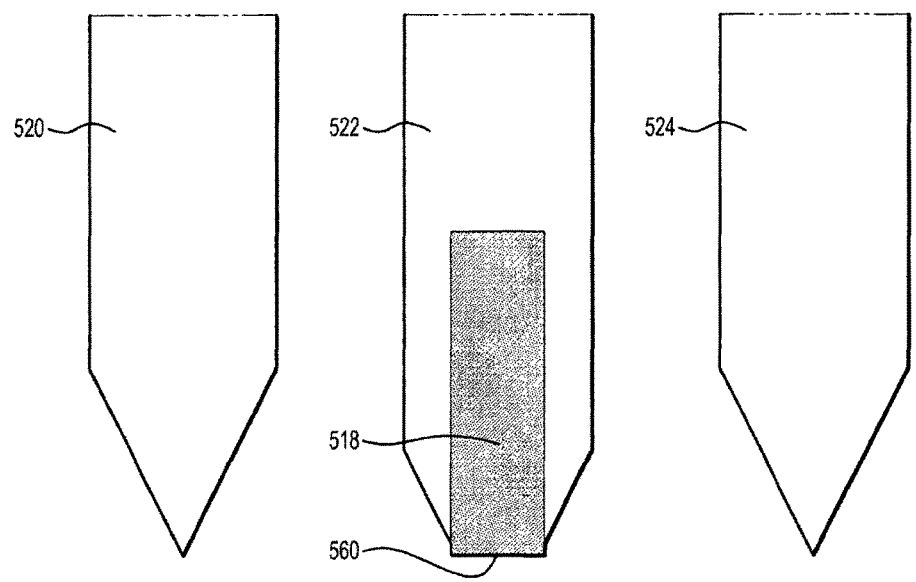

FIG. 3 schematically illustrates partial exploded views of two alternative embodiments of the microbiopsy device in whichthe plates would be overlaid to form the device.

FIG. 3 (a) shows a partial exploded view of a microbiopsy device 410 which includes an inner stainless steel plate 422 and two outer plates 420, 424 that each comprise transparent, medically approved glass or polymer, to facilitate visual inspection of the collected tissue in the chamber 418. The device 410 can be used to remove a small piece of skin and then immediately image the sample (such as by light microscopy, RCM, MPM or FLIM) without further preparation.

FIG. 3 (b) shows a further embodiment of a microbiopsy device 510 which includes two outer surgical grade stainless steel plates 520, 524 and an inner plate 522 that includes a chamber 518 in which is provided an absorbent membrane 560 for absorbing biological fluid, such as blood, plasma or serum, once the device is inserted into the skin. Alternatively, the inner plate 522 could be replaced entirely by a membrane of absorbent material.

Figure 10:
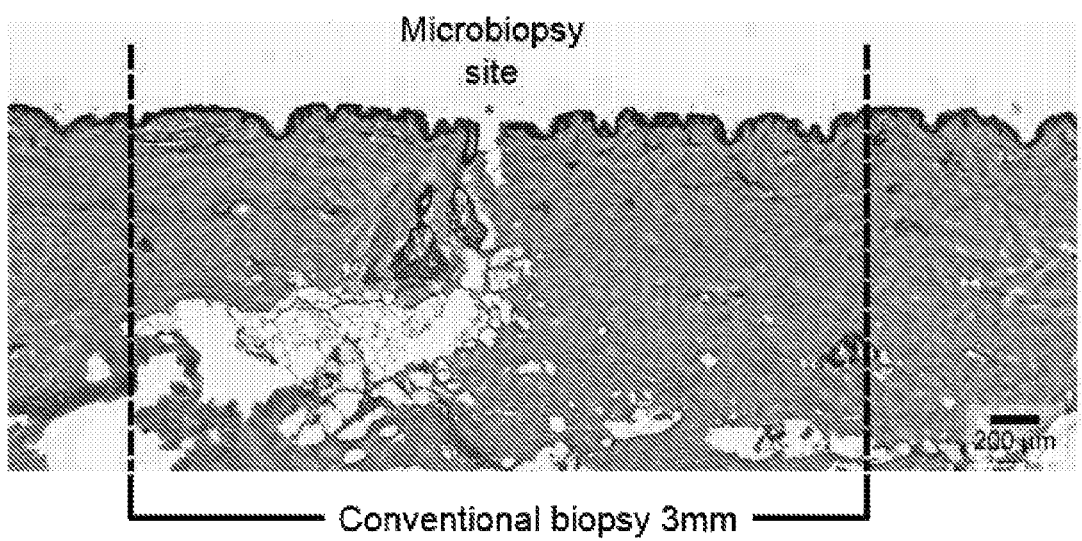
FIG. 10 is a histological section showing the comparison in size between the skin sample taken by conventional biopsy and that taken by the microbiopsy device of the disclosure.

FIG. 10 is a histological section showing the comparison in size between the skin sample taken by conventional biopsy and that taken by the microbiopsy device of the disclosure. The minimally invasive nature of the latter is clearly evident.

Figure 11:
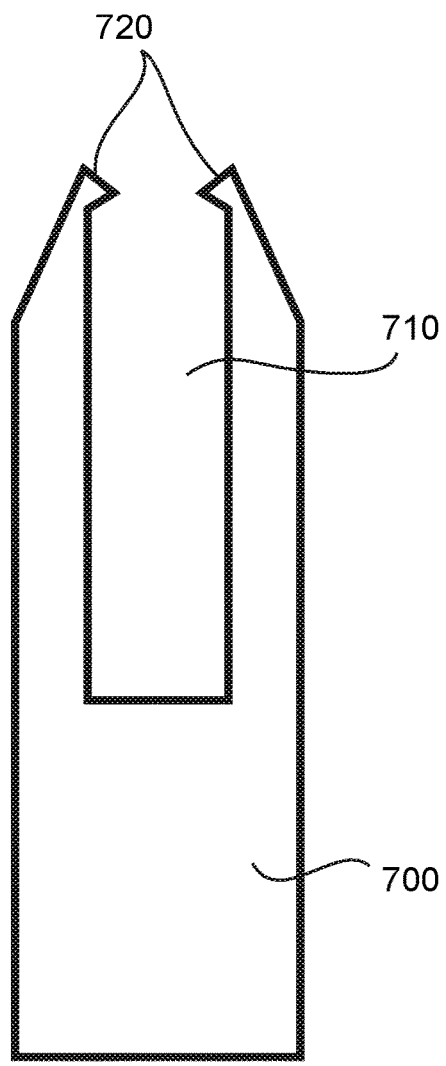
FIG. 11 illustrates an embodiment of a microbiopsy device according to the present disclosure.

FIG. 11 shows an embodiment of inner steel plate 700 of a microbiopsy device of the invention. Inner steel plate 700 comprises recess 710 which forms at least part of a chamber for receiving and/or retaining tissue of a microbiopsy device comprising inner steel plate 700. Inner steel plate 700 further comprises retaining elements 720 which are projections extending inwardly into recess 710. Retaining elements 720 are located at a position of recess 710 which forms at least part of the opening to the chamber of a microbiopsy device comprising inner steel plate 700.

EXAMPLES

Throughout the Examples, the results are expressed as mean±SD (standard deviation).

Example 1:

Chamber Width And Velocity Of Application

In a first example, a series of experiments were carried out to compare the amount of DNA extracted by microbiopsy devices having varying chamber widths and application velocity with the 0.15 mm chamber configuration. Each microbiopsy device comprised 3×50 µm thick stainless steel plates with the chamber is defined by an elongate recess (channel) in the inner plate.

Microbiopsy devices having of different channel widths (0, 0.1, 0.15, 0.2, 0.25, 0.3 mm) were applied to 20 healthy volunteers' volar forearms at a velocity of 20.2 m/s to determine the optimal chamber width. Similar procedures were performed for a device having a chamber width of 0.15 mm using an applicator having defined compression springs to achieve velocities between 0-20.2 m/s (n=20), ie at 1.1, 9.2, 16.6 and 20.2 m/s to is determine the optimal velocity. The applicator was purchased from Owen Mumford Ltd. Unistik 2, AT0700 (CAT#) and modified by removing the needle and replacing the spring with one having greater force. DNA was isolated from all microbiopsy samples and quantified using manufacturer's protocol. The results of the experiments are shown in FIG. 4.

Figure 4:
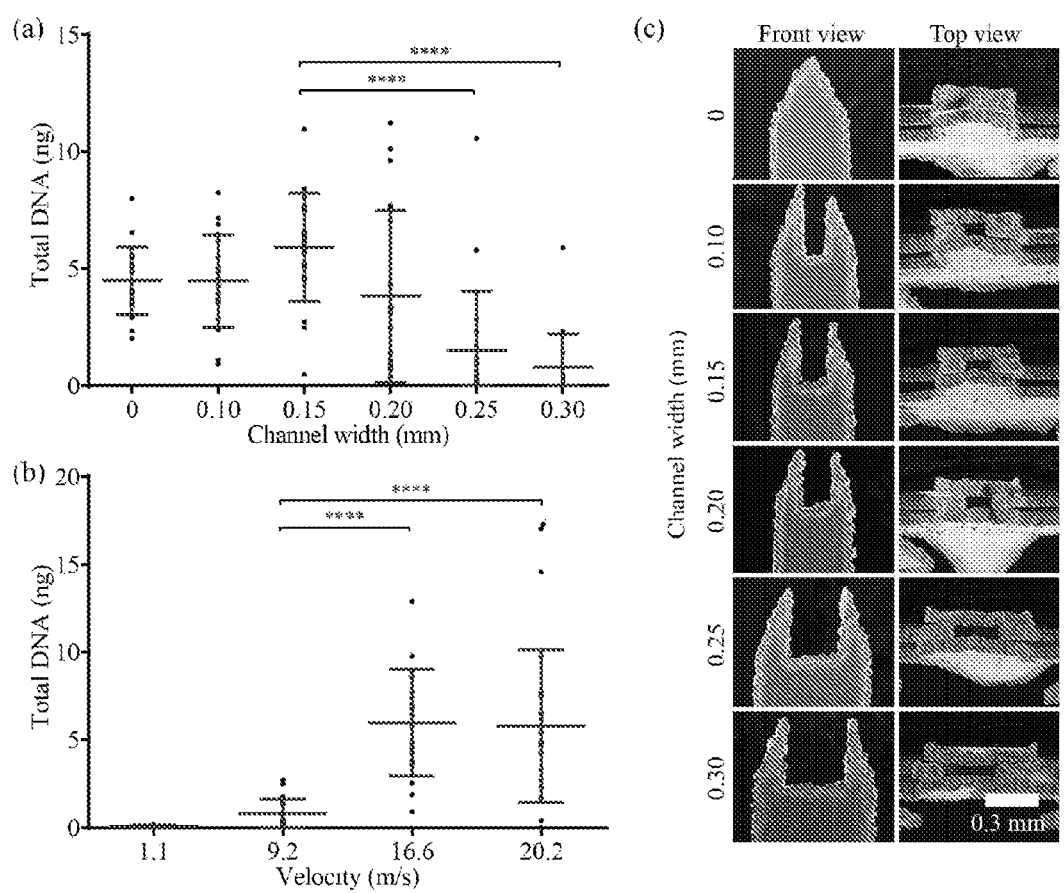
FIGS. 4 (a), (b) and (c) illustrate the results of Example 1 and are (a) a graph of the amount of DNA extracted (ng) versus width (mm) between opposed cutting elements; (b) a graph of the amount of DNA extracted (ng) versus impact velocity (m/s) of the device and (c) is electron micrographs of the devices.

FIG. 4 (a) shows the total extracted DNA (ng) for each channel width at a velocity of 20.2 m/s. FIG. 4 (b) shows that acceptable quantities of DNA were extracted at a channel width of 0.20 mm or lower when the device was applied at or over 16.6 m/s. The maximum amount of DNA was collected for a channel width of 0.15 mm. FIG. 4 (c) shows high resolution scanning electron microscopic images of the microbiopsy devices having different channel widths in the inner plate.

The results indicated that a channel width of 0.15 mm obtained the highest average amount of DNA (5.86±3.41 ng) and the optimal channel width was between 0.1 to 0.2 mm (n=20). Interestingly, tissue collection (4.48±1.45 ng) was observed around the rough edges of a microbiopsy device without a chamber (channel width of 0 mm). After the applying the microbiopsy, the device was opened up and visualized under a dissecting microscope. Successful collection was achieved when a piece of tissue was evident within the device and unsuccessful if no tissue was present. Tissue was collected from all volunteers (n=20) when a 0.15 mm channel width microbiopsy device was used. Only 13 successful collections were achieved from 20 applications when a 0.2 mm channel width microbiopsy device was used. This indicated that the collection rate decreased from 100% to 65% when channel width was increased by 0.05 mm. There was a trend in increase of amount of DNA extracted when channel widths were increased from 0 to 0.15 mm. The total amount of DNA decreased when channel width was wider than 0.15 mm. There was a significant decrease in total DNA when channel width was increased from 0.15 mm to 0.25 mm ($p<0.0001$). All other channel widths, including 0 mm, extracted significantly higher amount of total DNA compared to 0.25 mm and 0.3 mm microbiopsies ($p<0.05$). Data was analysed using One-way ANNOVA and Tukey post comparison statistical analysis techniques.

The results from microbiopsy application velocity tests indicated only negligible amounts of DNA were recovered when the device was applied at less than 9.2 m/s. However, there was a 7.5 fold increase (0.80±0.82 to 5.98±3.02 ng) in DNA recovered when the application velocity was increased from 9.2 m/s to 16.6 m/s ($p<0.0001$). An additional increase to 20.2 m/s in application velocity did not result in significantly increased DNA collection.

Example 2:

Pre-Application Compression Force

Figure 5:
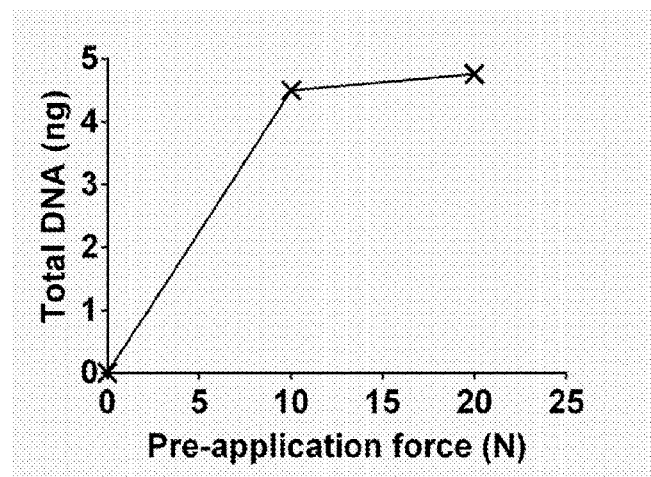
FIG. 5 illustrates the results of Example 2 and is a graph of the amount of DNA extracted (ng) versus pre-application compressive force (N).

In Example 2, a series of experiments were carried out to compare the amount of DNA extracted when a varied pre-application compression force was applied on the skin prior to using the microbiopsy devices. The experiments were conducted on one subject at 3 different forces. The pre-application skin compression forces that were tested were 0, 10 and 20N. In each case, the microbiopsy device comprised an assembly of three stainless steel plates, each plate being of 50 µm thickness. The impact velocity of the microbiopsy device was also kept constant at 15 m/s in all the experiments. FIG. 5 illustrates a graphical representation of the test results for Example 2. As shown in FIG. 5, a pre-application skin compression force of at least 10N was required to extract 4.5 ng of DNA. Furthermore, applying compression forces of greater than 10N did not lead to significant improvements in the amount of DNA extracted.

Example 3:

Surface Roughness Of Chamber

In Example 3, a series of experiments were carried out to compare the amount of DNA extracted when the surface roughness of the chamber walls was varied.

Identical microbiopsy devices comprising an assembly of three stainless steel plates, each plate being 50 µm thick, were used. The total width of the chamber of the device used was kept constant at 150 µm. All other device parameters were also kept consistent. The impact velocity was kept constant at 15 m/s and the pre-application skin compression force was also kept constant at 10N.

Figure 6:
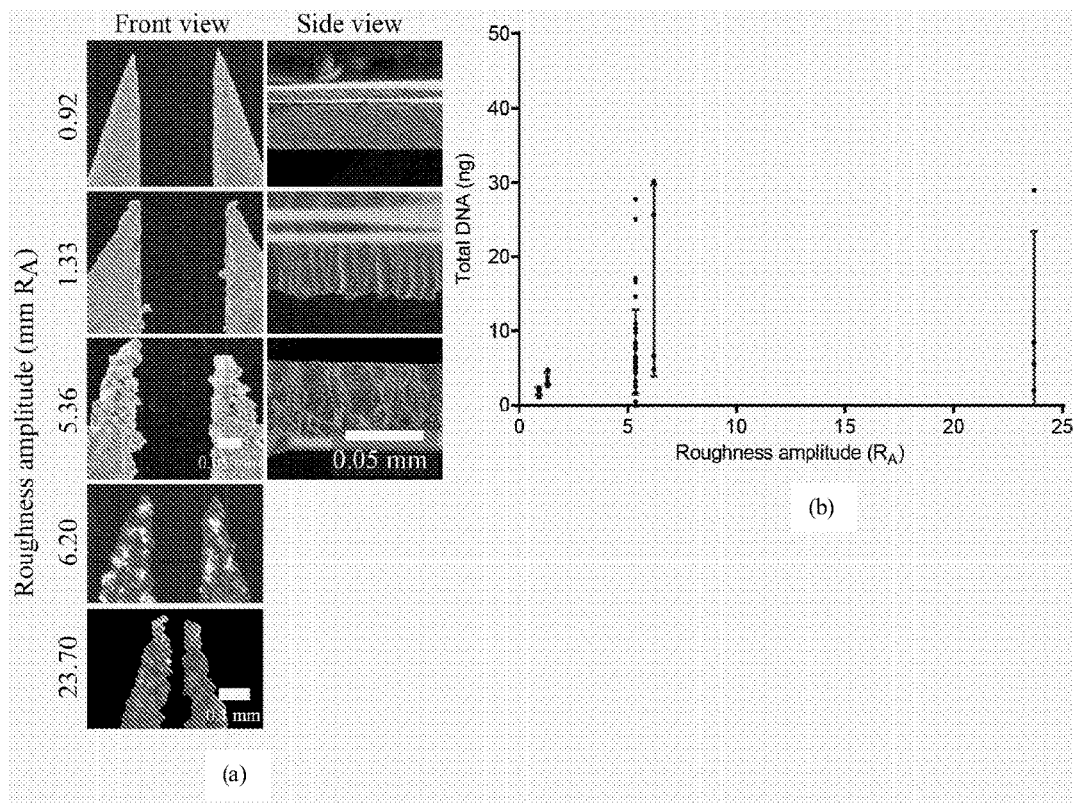
FIGS. 6 (a) and (b) illustrate the results of Example 3.

As described the surface roughness of the inner chamber of these devices were varied. The roughness amplitude of the microbiopsy chamber was obtained by measuring the average distances of the edge to a regression-fitted straight line using MatLab computing software. DNA was isolated from all microbiopsy samples and quantified using manufacturer's protocol. The results of these tests are shown in FIG. 6 $a$ (micrographs of microbiopsy devices having varying surface roughness) and FIG. 6$b$ (total DNA extracted versus $R_A$).

Initially, microbiopsy devices having roughness amplitude ($R_A$) ranging from 5.36 to 23.70 were tested. The higher roughness amplitudes (eg 23.70) were achieved by deliberately introducing jagged "teeth" on the chamber walls. Chamber walls with a low roughness amplitude (0.92) were generated by chemical milling. Greater roughness amplitude was observed when metal was cut using a laser cutter with a beam diameter of 10 µm (i.e. $R_A$=1.33). When a laser cutter with a substantially larger beam diameter was used (50 µm), $R_A$ was found to increase to 5.36, and was further increased by introducing small teeth ($R_A$=6.20) or jagged 'teeth' ($R_A$=23.7). An increase in total DNA extraction was observed when $R_A$ was increased from 5.36 to 6.20. The total DNA decreased when $R_A$ was further increased to 23.70. Subsequently, microbiopsy devices were fabricated that had is lower range of $R_A$ (0.92 and 1.33). The combined data showed that increasing the $R_A$ from 0.92 to 6.20 increased total DNA extraction by 8.6-fold (1.95±0.52 ng to 16.81±12.96 ng).

Accordingly, under the particular conditions of Example 3, it appeared that the optimal amount of sample retained in the chamber was at a surface roughness of around 6 µm of the chamber walls. Without wishing to be limited by theory, it is believed that there appear to be two opposing factors at work: the first factor being penetration depth of the cutting elements and the second factor being sample retention. It is theorized that rougher surface walls of the inner chamber will help to retain samples by friction but excessive roughness will reduce the surface area available for sample collection in the chamber.

Example 4:

Biological Fluid Extracting Microbiopsy Device

Figure 7:
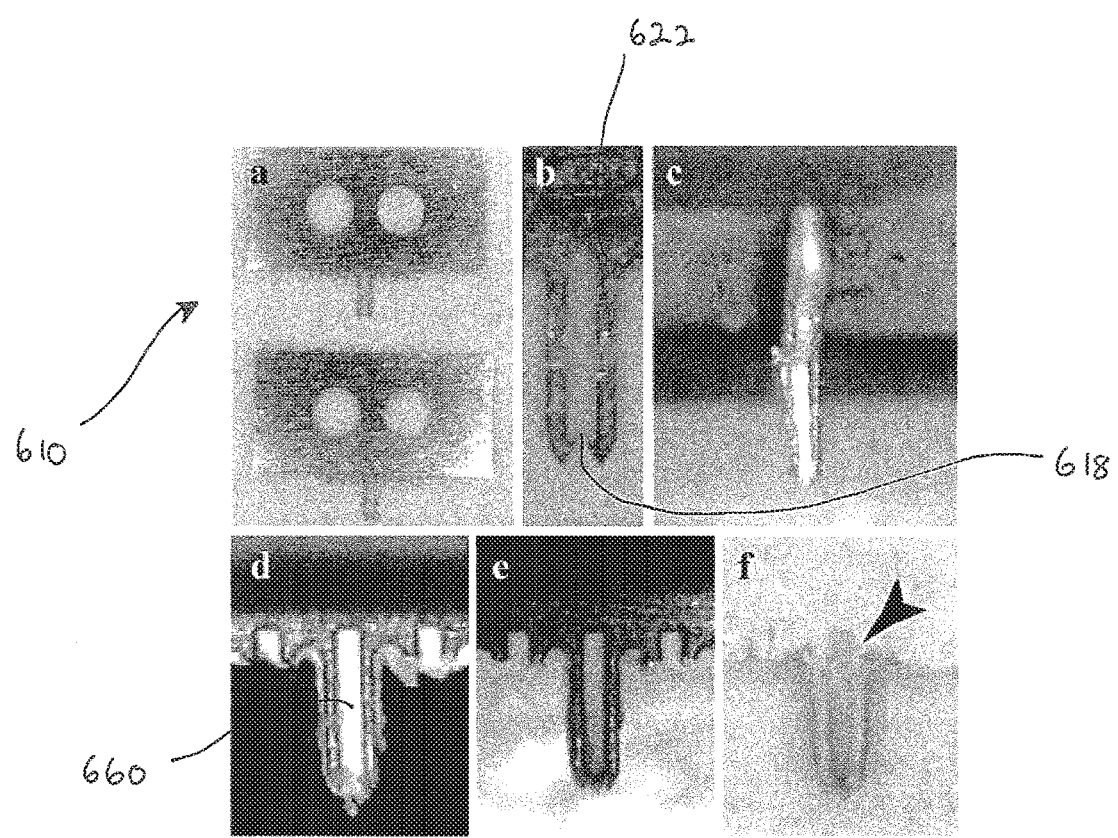
FIGS. 7(a) to (d) illustrate an embodiment of a microbiopsy device used in Example 4 and FIGS. (e) and (f) show the device after use in extracting biological fluid samples.

A Microbiopsy device 610 was fabricated having a partially open-sided chamber in which was provided an absorbent membrane for taking a sample of serum (FIG. 7$a$ to $d$). The device included a 50 µm thick stainless steel plate 622 having a recess 618 therein in which was received a 100 µm thick porous membrane 660 (FIGS. 7$c$ & $d$). The Microbiobsy device was applied to a patient's skin at a velocity of 6 m/s and left for 2 minutes in vivo. FIGS. 7$e$&$f$ show sera and blood absorbed into the membrane after removal of the device (7$e$&$f$, arrowhead in f).The sera was dried and stored for 2 days prior to running on a denaturing protein gel (µP) with size markers (M) and stock sera (1 µl and 2 µl).

Sera from mice infected with chikungunya virus (CHIKV) were extracted from the microbiopsy device into 45 µl of phosphate buffered solution (PBS) and was successfully used to identify the presence of anti-CHIKV antibodies in the sera using a fixed cell ELISA (Enzyme Linked Immuno Sorbent Assay).

Example 5:

Dna Extraction From Melanoma Lesions

Microbiopsy devices as illustrated in FIG. 1 were used to take tissue samples from melanoma lesions in mice. Each microbiopsy device included an assembly of 3 plates, with the chamber being defined by a recess in the inner plate. Total DNA was extracted and PCR analysis of all samples detected the NRAS mutation indicative of melanoma in the lesions.

Example 6:

Size Of Microbiopsy Defects

Figure 8:
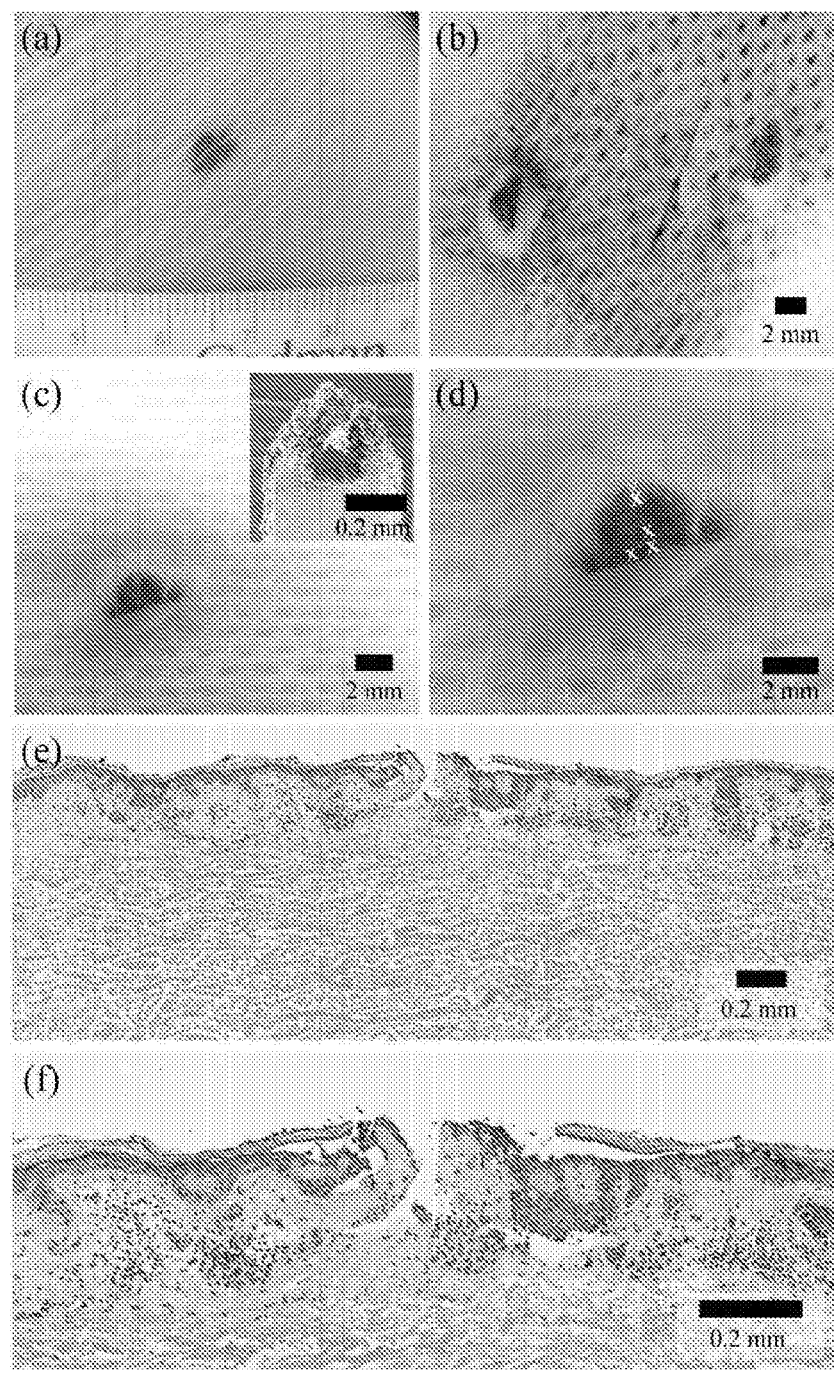
FIGS. 8 and 9 are clinical and dermoscopic images of melanocytic lesions as discussed in Example 6.
Figure 9:
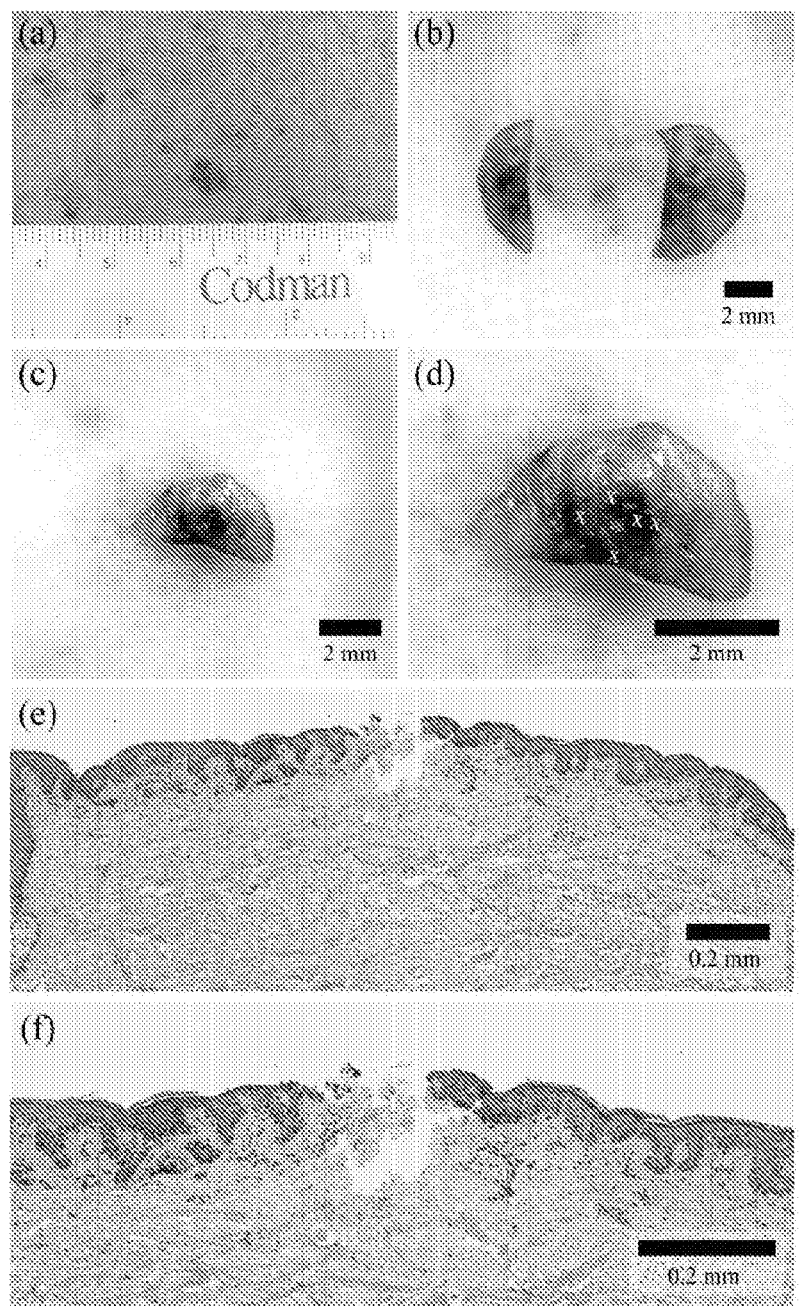

Clinical and dermoscopic images of suspicious melanocytic lesions from two patients were obtained before surgery and immediately after excision (FIGS. 8 and 9). Dermatoscopic images of excised lesions were also documented before and after application of the microbiopsy device to the lesion. Each excised lesion was cut in half and one half of the lesion was then chosen randomly to have five microbiopsies. Both halves were then placed in two different containers, pre-labelled with different codes. The samples were processed by a histopathologist and grading of defects was performed by 2 histopathologists.

FIG. 8 ($a$) shows a clinical photographs of a 6 mm atypical naevus found on the lower back of a 88-years old male patient. The excised lesion was cut into halves (FIG. 8$b$) and microbiopsies were taken on one half. The inset in FIG. 8 ($c$) shows a tissue sample contained in the microbiopsy device taken using a benchtop scanning electron microscope. The sites of the microbiopsy application cannot be seen with the naked eye even at a higher magnification. The locations of the microbiopsy sites were marked with white crosses in FIG. 8($d$). The site of microbiopsy was identified within the lesional region in the photomicrograph FIG. 8($e$) and the defect caused by the application of a microbiopsy demonstrated in a higher magnification photomicrograph (FIG. 8($f$) was approximately 50 µm×200 µm in size.

FIG. 9 $a$ is a clinical photograph showing a 6 mm atypical naevus found on the upper back of a 56-years old female patient. Similarly, the excised lesion was cut into halves FIG. 9(b) and microbiopsies were taken on one half FIG. 9(c). The sites of the microbiopsy application were also undetectable with the naked eye even at a higher magnification FIG. 9(d). The site of microbiopsy was outside the lesional region as shown in the photomicrograph FIG. 9(e) and the defect caused by the application of a microbiopsy demonstrated in a higher magnification photomicrograph (FIG. 9 (f)) was approximately 150 μm×200 μm in size.

Accordingly, these results indicate that the average dimensions of the identified microbiopsy defects were 112.83±50.28 μm wide and 145.7±36.66 μm deep. The defect caused by the microbiopsy application did not interfere with the diagnosis of the lesion.

Example 7:

Live Cell Imaging

The microbiopsy device was used to take tissue samples for use in live cell imaging, namely the ex vivo detection of reactive oxygen species (ROS). Microbiopsy tissue capture enables rapid live tissue analysis. In a clinical or experimental setting, skin can be treated and the microbiopsy used to extract living skin cells for analysis. In this example, volunteers were treated with topical cosmetic products and microbiopsy material tested for the presence or absence of oxidative stress. The cosmetic products were nanoparticle containing sunscreens.

Two commercial vital dyes were used in this example: CellROX and MitoSOX, both from Invitrogen. These dyes become fluorescent when oxidized. Confocal microscopy was used to observe the fluorescence intensity of microbiopsied skin.

Positive control samples, including porcine stable—equine kidney (PSEK) cells and microbiopsy samples, were treated with tert-Butyl hydroperoxide (TBHP) at 200 μM for 60 mins to induce ROS. All microbiopsy samples were obtained from a single volunteer. The samples were treated with a fluorogenic DNA dye using manufacturer's protocol. A nuclei counterstain was applied to the samples 10 mins before the imaging. A Zeiss Meta510 confocal microscope was used to obtain these images.

Both positive controls using PSEK cells and microbiopsy sample that were treated with TBHP were observed to have higher fluorescence signals compared to the negative controls. The conclusion of the experiment was that changes in oxidative stress could be detected using the microbiopsied material in conjunction with vital dyes and image analysis.

This Example shows the potential of the microbiopsy device as a tool to perform live cell assay in volunteers and animal models.

In the claims which follow, and in the preceding description, except where the context requires otherwise due to express language or necessary implication, the word "comprise" and variations such as "comprises" or "comprising" are used in an inclusive sense, i.e. to specify the presence of the stated features but not to preclude the presence or addition of further features in various embodiments of the device and method as disclosed herein.

The above references to the background art do not constitute an admission that the art forms a part of the common general knowledge of a person of ordinary skill in the art. The above references are also not intended to limit the application of the device and method as disclosed herein.

The invention claimed is:

1. A microbiopsy device for taking biological samples, comprising:
a body including two or more opposed, spaced cutting elements for cutting tissue to form a biological sample, wherein the cutting elements are arranged to cut a section of tissue having a width of less than 1 mm; and
an isolated chamber inside the body for receiving and retaining the biological sample, the isolated chamber having (a) an opening between the cutting elements for receiving the biological sample; (b) a closed end; and (c) one or more walls such that a retained biological sample is enclosed within the chamber except in the direction of opening between the cutting elements.

2. The microbiopsy device of claim 1, wherein the two or more opposed cutting elements together define at least one cutting edge.

3. The microbiopsy device of claim 1, wherein the two or more opposed cutting elements are arranged to cut a section of tissue having a width of 50-750 microns.

4. The microbiopsy device of claim 3, wherein the two or more opposed cutting elements are arranged to cut a section of tissue having a width of 100-200 microns.

5. The microbiopsy device of claim 1, wherein the section of tissue is noncircular.

6. The microbiopsy device of claim 1, comprising an assembly of at least two plates, wherein each cutting element is defined by a respective tapered section of one of said plates.

7. The microbiopsy device of claim 6, wherein the chamber is defined by one or more recesses in the plates.

8. The microbiopsy device of claim 1, wherein the chamber is configured to retain the biological sample therein by friction.

9. The microbiopsy device of claim 8, wherein at least one of the one or more walls has a surface roughness ($R_A$) of between 1 micron and 25 microns.

10. The microbiopsy device of claim 9, wherein a ratio of the surface roughness to a distance between at least two of the two or more opposed, spaced cutting elements is less than about 0.1.

11. The microbiopsy device of claim 1, further including retaining elements to retain the biological sample therein.

12. The microbiopsy device of claim 1, wherein the chamber has a non-circular cross section.

13. The microbiopsy device of claim 1, wherein the biological sample is of tissue or blood.

14. The microbiopsy device of claim 13, wherein the biological sample is of skin tissue.

15. The microbiopsy device of claim 1, comprising an insert for a punch biopsy applicator.

16. The microbiopsy device of claim 1, wherein the chamber has a width of 0.2 mm or less.

17. The microbiopsy device of claim 1, comprising at least four cutting elements.

18. The microbiopsy device of claim 17, comprising an assembly of at least three plates, each providing at least one cutting element, wherein at least one plate is an inner plate.

19. A method for making a microbiopsy device including the steps of:
providing at least two plates, each plate including a tapered section defining one or more respective cutting elements and at least one of the plates including a recess therein; and
forming an assembly of the plates such that:
the cutting elements are opposed and spaced from each other and together define a cutting end of the device for cutting tissue to form a biological sample, wherein the cutting elements are arranged to cut a section of tissue having a width of less than 1 mm; and the one or more recesses of the plates define an isolated chamber or receiving and retaining the biological sample having (a) an opening between the cutting elements; (b) a closed end; and (c) one or more walls such that a retained biological sample is enclosed within the chamber except in the direction of the opening between the cutting elements.

20. The method of claim 19, further including the step of forming the plates from a blank including panels corresponding to the plates.

21. The method of claim 20, wherein the step of forming the plates comprises folding the blank between the panels.

22. The method of claim 20, wherein the step of forming the plates comprises cutting the blank between the panels.

23. A blank for assembly into a microbiopsy device the blank including two or more panels, each panel having at least one tapered section and at least one of the panels having a recess, wherein upon assembly:

the tapered sections of the panels form at least two opposed, spaced cutting elements for cutting tissue to form biological sample, wherein the cutting elements are arranged to cut a section of tissue having a width of less than 1 mm; and the recess or recesses of the panels define an isolated chamber or receiving and retaining the biological sample having (a) an opening between the cutting elements; (b) a closed end; and (c) one or more walls such that a retained biological sample is enclosed within the chamber except in the direction of the opening between the cutting elements.

24. The blank of claim 23, wherein the blank comprises stainless steel.

25. A method for taking a biological sample from tissue, including the step of:
(i) applying a microbiopsy device to the tissue to cut the tissue, the microbiopsy device comprising: a body including two or more opposed, spaced cutting elements for cutting the tissue to form the biological sample, wherein the cutting elements are arranged to cut a section of tissue having a width of less than 1 mm; and an isolated chamber inside the body for receiving and retaining the biological sample, the chamber having (a) an opening between the cutting elements; (b) a closed end; and (c) one or more walls such that a retained biological sample is enclosed within the chamber except in the direction of the opening between the cutting elements; and
(ii) retaining the biological sample in the chamber of the microbiopsy device.

* * * * *

UNITED STATES PATENT AND TRADEMARK OFFICE
CERTIFICATE OF CORRECTION

PATENT NO. : 9,662,095 B2
APPLICATION NO. : 14/394907
DATED : May 30, 2017
INVENTOR(S) : Prow et al.

Page 1 of 1

It is certified that error appears in the above-identified patent and that said Letters Patent is hereby corrected as shown below:

On the Title Page

Change:
"(72) Inventors: Tarl W. Prow, Sunnybank (AU); H. Peter Soyers, Holland Park (AU); Alexander Bernard Ansaldo, Coorparoo (AU)"

To:
--(72) Inventors: Tarl W. Prow, Sunnybank (AU); H. Peter Soyer, Holland Park (AU); Alexander Bernard Ansaldo, Coorparoo (AU)--.

Signed and Sealed this
Twenty-third Day of April, 2019

Andrei Iancu
*Director of the United States Patent and Trademark Office*